March 22, 1966 H. A. JOHNSON, JR., ETAL Plant Pat. 2,611

STRAWBERRY PLANT

Filed April 21, 1964

INVENTORS
Harold A. Johnson, Jr.
BY Harold E. Thomas
Townsend and Townsend
attorneys United States Patent Office Plant Pat. 2,611
Patented Mar. 22, 1966

2,611
STRAWBERRY PLANT

Harold A. Johnson, Jr., and Harold E. Thomas, Morgan Hill, Calif., assignors to The Strawberry Institute of California, Morgan Hill, Calif.

Filed Apr. 21, 1964, Ser. No. 361,602
1 Claim. (Cl. Plt.—49)

This invention relates to a new and distinct variety of strawberry plant which is the result of a cross between two Strawberry Institute of California seedling selections numbered E101.10 and C52.3 (both unpatented).

Seedlings resulting from this cross were grown and held in an isolated area near Big Bend, California, and were there asexually reproduced by means of transplanted runners. Testing of the asexually reproduced plants has been carried out in various parts of California.

Figure 1:
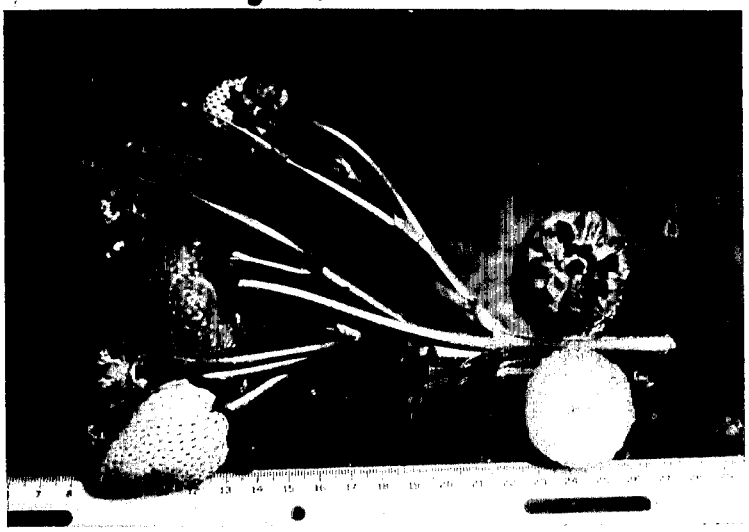
Figure 2:
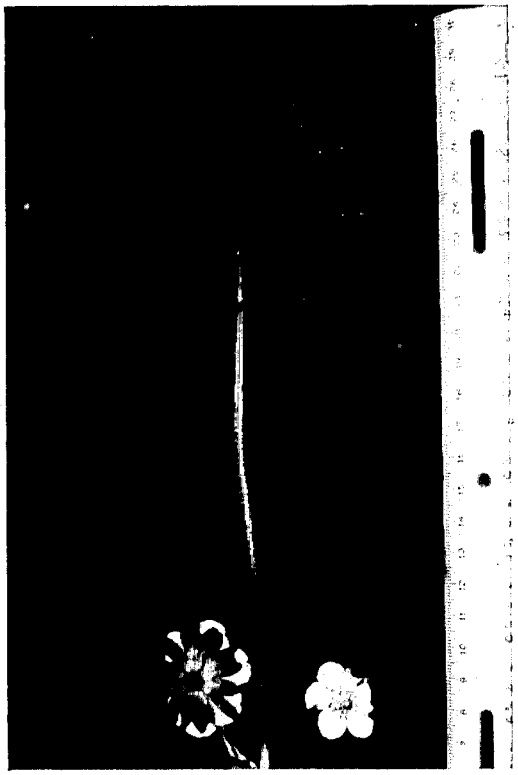

A plant typical of the size, shape and color of the new variety is shown in the accompanying drawing in which:

FIGURE 1 shows (a) a typical inflorescence with a primary and a secondary berry, (b) a cross section of a typical ripe berry and (c) the base of a typical ripe berry with the calyx attached; and FIGURE 2 shows (a) a typical leaf, and (b) a top view and an underview of a typical blossom.

A distinguishing characteristic of this new plant is its squat appearance due to its tendency to grow prostrate rather than upward. This tendency to prostrate growth is in contrast to the upward growth habit of the Goldsmith variety described in Plant Patent No. 1,735. Also giving this new variety a squat appearance is the tendency of the leaves to cup downward. The leaf petioles are slightly larger than found in the Goldsmith variety, but the leaf blades are slightly larger on the average and have a less rugose surface.

This new variety is an open crown type of medium size and vigor. The color of the foliage is slightly lighter than that of the Goldsmith variety with the contrast becoming even more noticeable as the season progresses. Further contrast in foliage color between this new variety and the Goldsmith variety is the lack of purpling of the foliage late in the season in this new variety. This new variety is very low in runner production and there is some difficulty in the nursery in obtaining a satisfactory reproduction ratio.

Another characteristic distinguishing this new variety from most other varieties is the production of split fruit in the primary berries of the summer crop. In spite of this deformity in the fruit which requires the discarding of a portion of the summer crop, the total annual yield of marketable fruit remains high and equals or excels other everbearing varieties. The fruit is at times somewhat blotched in color. The fruit is borne on a comparatively long inflorescence in much the same way as the fruit is borne in the Goldsmith variety. The fruit of this new variety is large and packs reasonably well in a shipping crate in spite of the fact that the surface is more irregular and less smooth than that of the Goldsmith variety. This new variety has the ability to produce good-sized fruit in the early spring or crown crop, a characteristic not common to all everbearing strawberry plants. The fruit of this new variety appears to be relatively free of the summer deformity common to some of the standard varieties grown in California. This may be a result of the abundance of pollen which is produced by this new variety. The fruit cavity is smaller in size than that of the Goldsmith variety. The core is easily removed and in picking often comes out with the calyx unless the picker is careful in snapping off the fruit. On the average the calyx is smaller than the calyx of the Goldsmith variety and is more apt to have overlapping sepals. The skin of the fruit of the new variety is relatively firm and tough which gives it the ability to be transported to distant markets with assurance of good arrival.

This new variety has the typical everbearer type of production wherein spring production is relatively low with the main crop starting in early summer and continuing until frost with peaks in production occurring during this period. The plant will produce well in its second year but the crops start late and the fruit is somewhat smaller in size than that produced in the first year.

The dessert quality of the fruit of this new variety is good and is about equal to that of the Goldsmith variety.

This new variety has no particular weaknesses to strawberry virus diseases but has not yet been thoroughly tested. It is susceptible to Verticillium wilt. It is affected by two-spotted mite but no more so than most of the standard varieties grown in California.

For convenience the characteristics of this new variety of strawberry plant as observed in the Monterey Bay area of California are summarized as follows:

*Plant characteristics*

*Foliage.*—The foliage is of small to medium size, is of an open crown type and is characterized by a semi-prostrate type of growth. The vigor of the foliage rates from moderate to low. The plant will not grow satisfactorily in saline soils.

*Root system.*—The root system is of medium size and vigor.

*Leaves.*—The leaves are medium in size with a central leaflet diameter of 5.5 to 8.5 centimeters. The length is slightly greater than the width. Leaflets generally are held low and parallel to the ground with the margin cupped slightly downward. The leaves are generally flat and smooth and only slightly rugose. The serrations on the margins of the leaflets are ovate with an acute apex. The apex usually turns downward as the leaf ages. The leaflets tend to fade in color with age. The color of the upper side of the mature leaf is Elm Green as shown on Plate XVII of Ridgway's Color Standards and Nomenclature (1912 edition). The color of the lower side of the mature leaf is Bice Green as shown on Plate XVII of Ridgway.

*Petioles.*—The petioles are of medium length, usually from 12 to 18 centimeters in average growth plants. Bracts may be present.

*Runners.*—Fruiting bed runner production is poor to medium. A ratio of ten to fifteen daughter plants to one mother is normal in the nursery.

*Inflorescence.*—The inflorescences are medium in length, being mostly between fifteen and twenty-five centimeters. Then length varies during the season. In most inflorescences the pedicel of the primary berry and the peduncles of the secondary berries originate from a common axil on the main fruiting stem. The hair on the tertiary pedicel 20 millimeters below the flowers lays irregularly against and parallel with the pedicel. Bloom is visible above the plant early in the season but is normally hidden in later crops. This new variety is a good pollen maker.

*Fruit characteristics*

*Size.*—The primaries and well developed secondaries are mostly large, averaging 40 to 45 millimeters in length. The width is usually slightly less.

*Shape.*—The shape varies between long conic and long wedge. There is a tendency to develop split fruit on the primaries of the main summer crop. Split berires are seldom formed during the spring crown crop.

*Surface.*—The surface may be iregular with shallow furrows lying the length of the fruit. At times there is some taper to the shoulders but there is no tendency to become necked.

*Color.*—The surface color of the fruit grades from Scarlet Red to Nopal Red as shown on Plate I of Ridgway. The color is glossy. The fruit may ripen irregularly with a tendency to produce blotches on the surface, especially on the calyx end. The inside berry color is scarlet at the periphery grading to a light pink at the center.

*Core.*—The berry is mostly solid with only a small cavity in the larger fruit. The berry has a small core which is easily pulled out with the calyx.

*Flavor.*—The flavor is considered as mild and is subacid and the same generally as Goldsmith, supra. There is no particular aroma to the flesh.

*Flesh.*—The flesh is firm but juicy.

*Seeds.*—The seeds are medium in size and are generally held even with the surface. At times the seeds may be slightly below or slightly above the surface. The green fruit produces seed that is noticeably dark against the light surface of the fruit. The seed color on the unexposed side of the ripe fruit is Apricot Yellow as shown on Plate IV of Ridgway. The exposed seeds are dark in color.

*Calyx.*—The calyx is medium large with a diameter usually from 30 to 35 millimeters. The sepals are narrow and of lanceolate to linear shape, alternating slightly in size. Many calyxes have sepals that overlap somewhat with the small overlapping the large. The sepals have a pointed apex and a few may be serrated. The calyx is generally held irregularly free of the fruit surface.

The plant above described may vary in slight detail depending upon the climate, the soil and other growth conditions.

We claim:

A new and distinct variety of strawberry plant as herein described and illustrated and characterized particularly by its medium size and prostrate type of growth, by its large fruit size of conic to wedge shape and its tendency to split primaries in the summer crop, and by its ability to produce a large crop of fruit with firm skin and flesh.

No references cited.

ABRAHAM G. STONE, *Primary Examiner.*